US00PP15659P2

(12) United States Plant Patent
Friday

(10) Patent No.: US PP15,659 P2
(45) Date of Patent: Mar. 15, 2005

(54) PEACH TREE NAMED "P.F. 24-C COLD HARDY"

(50) Latin Name: *Prunus persica*
Varietal Denomination: P.F. 24-C cold hardy

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 11 days.

(21) Appl. No.: 10/832,834

(22) Filed: Apr. 27, 2004

(51) Int. Cl.[7] ..... A01H 5/00
(52) U.S. Cl. ..... Plt./198
(58) Field of Search ..... Plt./198

*Primary Examiner*—Anne Marie Grunberg

(57) ABSTRACT

A new and distinct variety of peach, *Prunus persica,* tree having the following unique combination of desirable features:

1. Producing a bud that is particularly winter and spring cold hardy.
2. The limbs of the tree naturally grow at wide angles creating a wide-spreading tree.
3. A fruit with a smooth raised suture that remains firm as does the whole fruit.
4. A late maturing, highly colored, peach cultivar that matures a few days before the old standard variety, "Cresthaven" (unpatented), and which hangs on the tree for many days, staying extremely firm.

1 Drawing Sheet

Botanical classification: *Prunus persica.*

ORIGIN OF VARIETY

The new peach tree {hereinafter referred to as the 'P.F. 24-C cold hardy' peach tree} was originated by Paul Friday in the experimental orchard, which is maintained for the purposes of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollinations of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 24-C cold hardy', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of characteristics of the tree are consistent and established and transmitted through succeeding propagation.

SUMMARY OF THE VARIETY

The new and distinct variety of peach tree is of average height and of spreading growth and a regular and productive bearer of peaches. A distinct characteristic of the "P.F. 24-C cold hardy" peach tree is its medium vigor having a growth of about eighteen inches (18") per year. The blossoms bloom in mid-season and are characterized by being contracted or partially spread to approximately ⅝-inch when in full bloom. At the same time the five petals of the blossoms are of lesser length than the length of petals of the normal showy blossom as exemplified by the 'Loring' (unpatented) peach blossom.

The blossoms of the present peach tree at full bloom may be characterized as being non-showy. More specifically, the blossoms of the present peach tree have radially projecting and angularly spaced five blossom petals to form a blossom having a diameter of about ⅝-inch measured across the blossoms.

The flesh of the fruit of the present peach tree is extremely firm and is yellow.

The skin is smooth having moderate to little down and is of dark red color overlying a yellow ground color. The yellow background covers approximately thirty percent (30%) of its surface at maturity. At maturity, the peach is spherical having an average diameter of about 2¾".

The fruit produced by this tree has firm, and non-melting flesh, and thereby has the attendant resistance to blemishes and soft spots in harvesting, shipping and handling due to bruising, The firmness of the fruit flesh is sufficient to allow the flesh to yield and be restored when bumped or dropped without the resulting soft spots as would be experienced in most late season peaches of the market class. Thus, fruit of this tree remains more attractive to the ultimate buyer, the consumer, and thereby will command premium prices for late fresh desert market.

The fruit matures in the latter part of the peach growing season in southwestern Michigan. The fruit as mentioned heretofore is of dark red color overlying a yellow which covers approximately Thirty percent (30%) of its surface and has a very attractive appearance.

BRIEF DESCRIPTION OF THE PHOTOGRAPHS

The top photograph shows the leaves of the plant both upper and lower side.

The bottom photograph shows two (2) whole peaches of this cultivar depicting dark red skin color for fruit maturing so late in the season. The middle fruit has been split on a plane ninety degrees to the suture plane to depict the fruit flesh in cross section. The conformance of the pit cavity is illustrated, as is the desirable ratio of the size of the stone to the fruit size of this tree. A ruler has been placed in the photograph showing the large size of the fruit.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System {PMS} as used internationally to identify printed colors.

Botanical classification: *Prunus persica* cultivar 'P.F. 24-C cold hardy'.

Tree:
- *Age.*—Seven (7) years.
- *Height.*—Unpruned 12'.
- *Width.*—Unpruned 10'.
- *Size.*—Medium.
- *Vigor.*—Medium.
- *Density.*—Medium.
- *Form.*—Spreading natural wide angle crotches.
- *Production.*—Good, about ⅔ of the fruit must be thinned off of the tree annually.
- *Bearer.*—Extradornally consistant.
- *Disease resistance to bacterial leaf and fruit spot.*—Very resistant.

Trunk:
- *Bark.*—Dark gray (418).
- *Size.*—Medium to Large.
- *Surface.*—Rough.
- *Diameter.*—5" diameter 18" above the ground at 7 years of age.
- *Lenticels.*—Pronounced.
- *Lenticels color.*—400.
- *Lenticels size.*—⅜".

Branches:
- *Size.*—Medium 2" diameter 5" from trunk.
- *Surface.*—Semi Rough.
- *Lenticels per square inch.*—Eight (8).
- *Lenticels color.*—400.
- *Lenticels size.*—3/16".
- *Crotch angles.*—Natural right angles.
- *Branch color.*—Gray (436).
- *Internode length.*—¾".

Leaves:
- *Size.*—Average length 7¼" average width 1½".
- *Form.*—Lanceolate.
- *Thickness.*—Medium.
- *Texture.*—Glabrous.
- *Margin.*—Serrate.
- *Petiole length.*—⅜".
- *Number of glands.*—Uniquely one on each side of top part of petiole, occassionally an additional One or two on the basil part of leaf.
- *Gland shape.*—Slightly elongated, very shallow.
- *Gland color.*—Reddish brown.
- *Leaf color.*—Upper surface green (364) — lower surface green (378).

Flowerbuds:
- *Size.*—7/16" long — ¼" wide.
- *Bud shape.*—Ovid.
- *Bud color.*—223.

Flowers:
- *Blooming period.*—Apr. 25, 2003 to Apr. 30, 2003.
- *Bloom size.*—⅞" diameter.
- *Size of petals.*—⅜" long — ¼" wide.
- *Shape of petals.*—Cupped.
- *Petal color.*—250.
- *Sepal size.*—3/16" long — 3/16" wide.
- *Sepal shape.*—Cupped.
- *Sepal color.*—417.
- *Number of anthers.*—32.
- *Anther color.*—125.
- *Number of stamens.*—32.
- *Stamen length.*—¼".
- *Stamen color.*—417.
- *Pistil length.*—5/16".
- *Pistil color.*—388.
- *Pollen.*—Present.
- *Number of petals.*—Five (5).
- *Flower color.*—250.
- *Number flowers per cluster.*—2.
- *Fragrance.*—Pleasant.

Fruit:
- *Maturity when described.*—Firm ripe.
- *Date of first picking.*—Jul. 22, 2003.
- *Date of last picking.*—Aug. 7, 2003.
- *Size.*—Average 2¾".
- *Form.*—Ovid.
- *Suture.*—Not pronounced.
- *Weight.*—6.9 oz.

Skin:
- *Thickness.*—Medium.
- *Texture.*—Medium.
- *Tendency to crack.*—None.
- *Down.*—Light.
- *Color.*—About 90% red (187) over dark yellow (143).

Flesh:
- *Texture.*—Firm.
- *Ripens.*—Even.
- *Flavor.*—Very good.
- *Aroma.*—Pleasant, mild.
- *Eating quality.*—Excellent.
- *Color.*—Deep yellow (136).
- *Pit cavity color.*—Red (179).

Stone:
- *Type.*—Freestone.
- *Size.*—1½" long, 1⅛" wide, 11/16" thick.
- *Form.*—Ovid.
- *Base.*—Straight.
- *Apex.*—Pointed.
- *Sides.*—Nearly equal.
- *Surface.*—Furrowed.
- *Color.*—Reddish brown (478).
- *Tendency to crack.*—5%.
- *Kernel.*—¾" long — 7/16" wide — 1/16" thick. No chilling requirement data available at this time.

Use: Desert.
Shipping quality: Very good.
Keeping quality: Very good.

The tree and its fruit herein described may vary slight as a result of differences in climatic or soil conditions or cultural practices under which the tree may be grown. It is understood that the description of the new variety as set forth herein is that of the tree grown under the ecological conditions prevailing at Coloma, Mich.

What is claimed is:

1. A new and distinct variety of peach tree as herein illustrated and described wherein the tree is a particularly cold hardy freestone peach maturing in the late season ripening a few days before 'Cresthaven' (non-patented) peach variety and producing large freestone highly colored and firm maturing fruit.

* * * * *

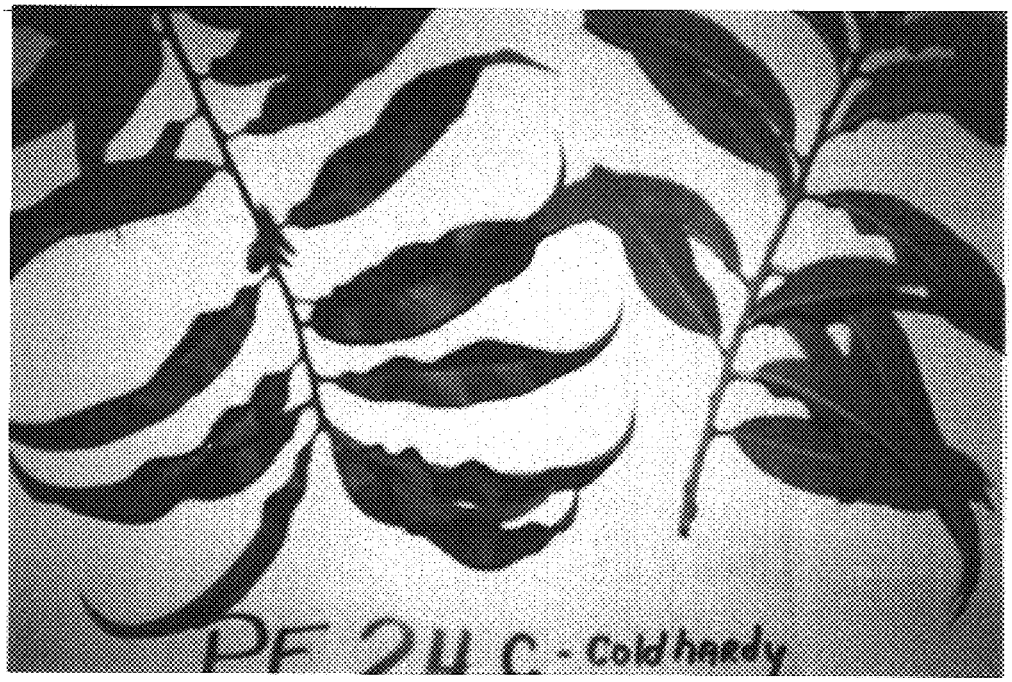
PF 24 C - Coldhardy
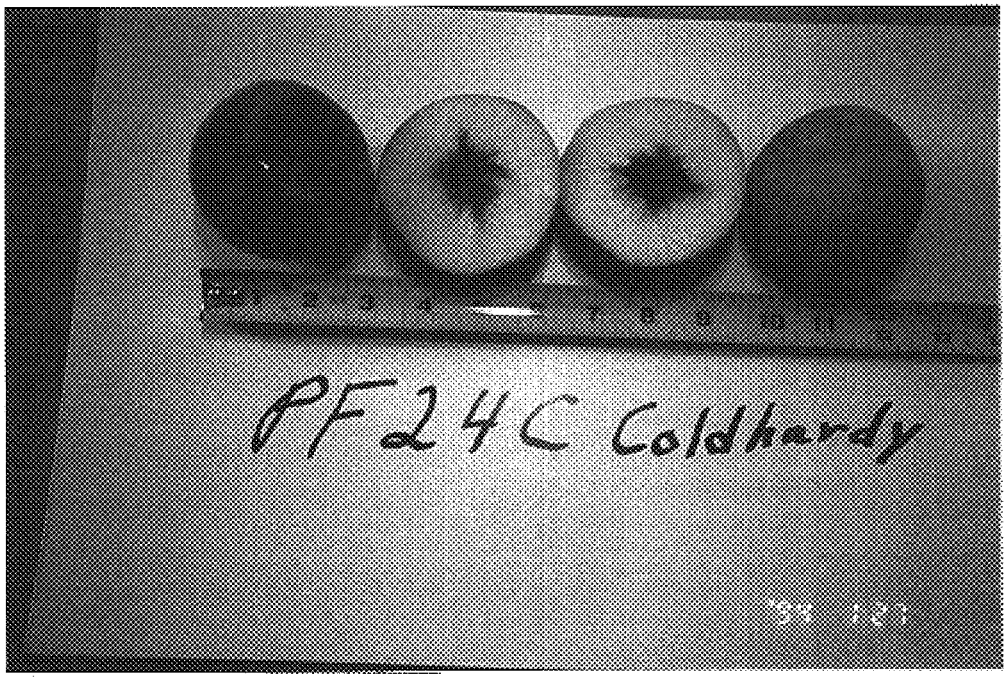
PF24C Coldhardy